United States Patent [19]

Kuroiwa et al.

[11] Patent Number: 5,399,488
[45] Date of Patent: Mar. 21, 1995

[54] METHOD FOR ASSAYING ENZYME ACTIVITY USING N-ACETYL-$\beta$-D-GLUCOSAMINE DERIVATIVES

[75] Inventors: Katsumasa Kuroiwa; Katsuhiro Katayama; Toshihide Miura, all of Koriyama; Takeshi Nagasawa, Urawa, all of Japan

[73] Assignee: Nitto Boseki Co., Ltd., Fukushima, Japan

[21] Appl. No.: 248,856

[22] Filed: May 23, 1994

Related U.S. Application Data

[63] Continuation of Ser. No. 919,521, Jul. 24, 1992, abandoned.

[30] Foreign Application Priority Data

Aug. 1, 1991 [JP] Japan ................. 3-193152

[51] Int. Cl.$^6$ .............. C12Q 1/34; C07H 5/10; C07H 17/02; C07H 19/048
[52] U.S. Cl. ........................ 435/18; 435/4; 536/17.3; 536/17.4; 536/17.5; 536/17.6; 536/17.2; 536/1.11; 536/4.1; 536/55.2
[58] Field of Search ............... 435/18, 7.72, 4; 536/17.3, 17.4, 17.5, 17.6, 17.2, 1.1, 4.1, 55.2

[56] References Cited

U.S. PATENT DOCUMENTS

| | | | |
|---|---|---|---|
| 4,433,139 | 2/1984 | Ogawa et al. | 536/17.2 |
| 4,552,841 | 11/1985 | Ogawa et al. | 435/18 |
| 4,754,025 | 6/1988 | Makise et al. | 536/17.7 |
| 5,030,721 | 7/1991 | Kasai et al. | 536/4.1 |
| 5,126,329 | 6/1992 | Tani et al. | 514/25 |
| 5,155,026 | 10/1992 | Noto et al. | 435/18 |

FOREIGN PATENT DOCUMENTS

216466A1 12/1984 German Dem. Rep. ...... C07H 5/08
217224A1 1/1985 German Dem. Rep. .... C07H 13/00

OTHER PUBLICATIONS

Abramovitch, R. A., ed., "Pyridine and Its Derivatives", 1975, (supplement to The Chemistry of Heterocyclic Compounds, vol. 14), pp. 248-249.
Robinson, D. et al., "Separation and Properties . . . ", Biochem. J., (1967), 102, 525-532.
The Merck Index, 1983, pp. 1407-1408.
S. J. Christopher et al., Dept. of Biol. Chem., 255, 1861-1869 (1980).
Price and Robinson, Comp. Biochem. Phyisol., 1966, 17, 129-138.
Leaback and Walker, Biochem. J., 1961, 78, 151-156.
Method of Enzymatic Analysis, Third Edition, vol. IV, 269, (1984), p. 274.

(List continued on next page.)

Primary Examiner—Douglas W. Robinson
Assistant Examiner—Francisco C. Prats
Attorney, Agent, or Firm—Darby & Darby

[57] ABSTRACT

Novel N-acetyl-$\beta$-D-glucosamine derivatives and a method for assaying N-acetyl-$\beta$-D-glucosaminidase activity using the same as substrate are provided.

N-Acetyl-$\beta$-D-glucosamine derivatives represented by general formula (I):

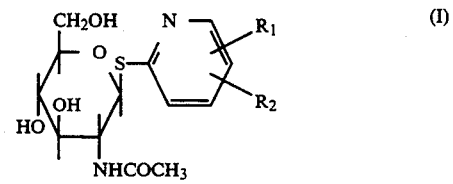

wherein each of $R_1$ and $R_2$ independently represents hydrogen atom or methyl or ethyl group, are mixed with a sample containing N-acetyl-$\beta$-D-glucosaminidase (NAG) and then absorbance of the reaction solution is determined to assay NAG activity extremely accurately.

6 Claims, 9 Drawing Sheets

OTHER PUBLICATIONS

D. Piszkiewicz et al., *J. Am. Chem. Soc.*, 89, 6237–6243 (1967).
Chemical Abstract of G. Wagner, *Naturwissenschaften*, 52, 83–84 (1965).
Chemical Abstract of G. Wagner et al., *Pharmazie*, 20, 752–757 (1966).
N. Dance et al., (1969), *Clin. Chim. Acta*, 24, pp. 189–197.
C. T. Yuen, (1982), *Clin. Chim. Acta.*, vol. 124, pp. 195–204.
E. Horak et al., *Clin. Chem.*, vol. 27(7), pp. 1180–1185.
A. Noto et al., (1983), *Clin. Chem.*, vol. 29(10), pp. 1713–1716.
J. Makise, (1988), *Clin. Chem.*, vol. 34(10), pp. 2140–2143.
I. Pocsi, (1990), *Clin. Chem.*, vol. 36(11), pp. 1884–1888.
K. Sasamoto, (1990), *Analytical Sciences*, vol. 6, pp. 145–148.
K. Sasamoto, (1991), *Analytical Sciences*, vol. 7, pp. 333–335.
Kiki/Shiyaku, vol. 13, pp. 887–893 (1990).

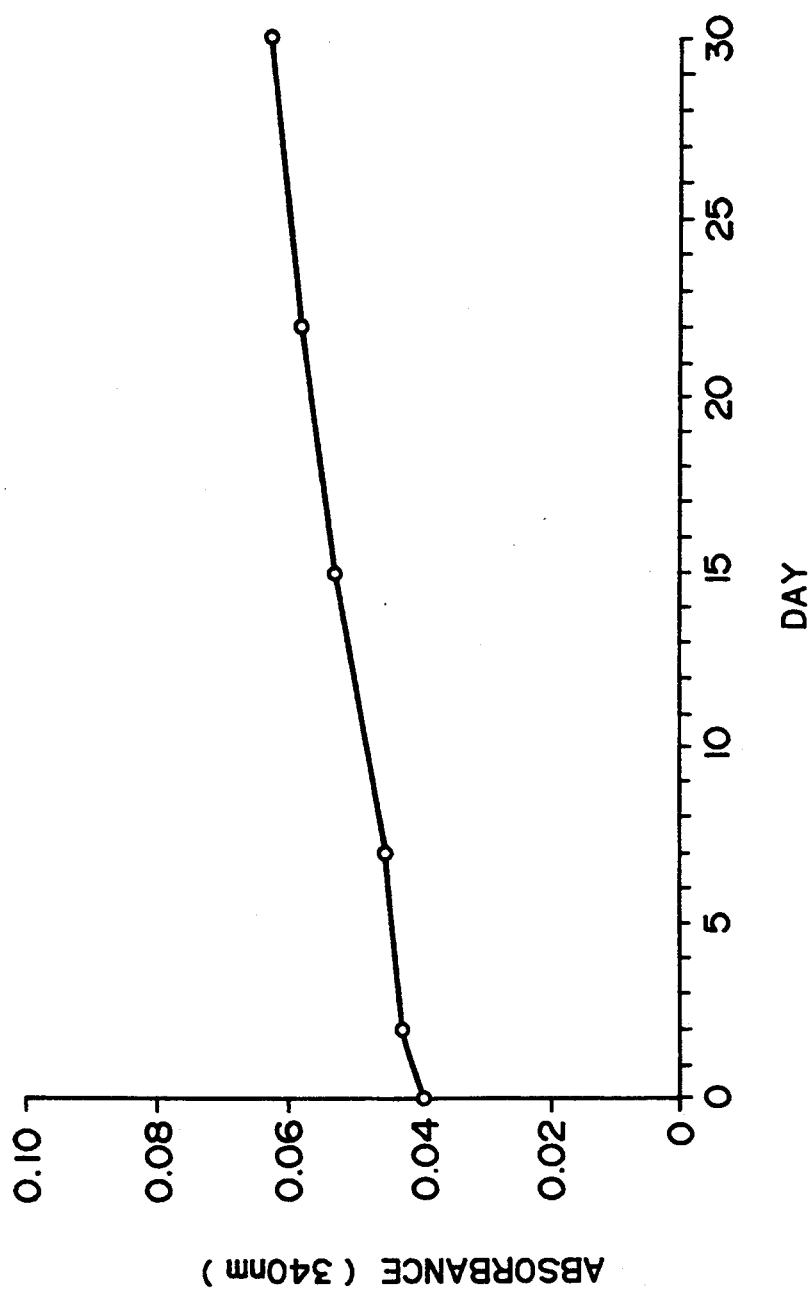

METHOD FOR ASSAYING ENZYME ACTIVITY USING N-ACETYL-β-D-GLUCOSAMINE DERIVATIVES

This is a continuation of application Ser. No. 07/919,521, filed Jul. 24, 1992, now abandoned.

FIELD OF THE INVENTION

The present invention relates to novel N-acetyl-β-D-glucosamine derivatives represented by general formula (I):

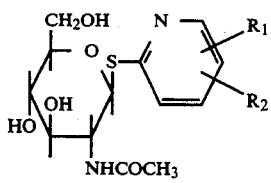

wherein each of $R_1$ and $R_2$ independently represents hydrogen atom or methyl or ethyl group, and a method for assaying N-acetyl-β-D-glucosaminidase activity using the same as substrate.

According to the present invention, N-acetyl-β-D-glucosaminidase activity can be determined accurately in a simple manner and is extremely important in the field of medical treatment and clinical inspection as a method for determination of N-acetyl-β-D-glucosaminidase activity.

RELATED ART STATEMENT

N-Acetyl-β-D-glucosaminidase (hereafter abbreviated as NAG) is a lysosomal enzyme derived from the proximal kidney tubule. This enzyme is released in urine by disturbance of kidney tubule and is thus an index of renal impairment. It is also known that NAG activity in urine increases in various renal diseases such as drug-induced renal disturbance, nephrosis syndrome, glomerulonephritis, etc. It is said that in diabetic nephritis, NAG increases not only in urine but also in serum and the enzyme is thus utilized for early diagnosis of these diseases.

For determination of NAG activity, methods using various synthetic substrates are reported as shown below and some of the methods are practically used in ordinary clinical inspection.

(a) Method using 4-methylumbelliferyl-N-acetyl-β-D-glucosaminide as substrate

Fluorescent intensity of 4-methylumbelliferone formed by hydrolysis of NAG is measured by a fluorophotometer [Clin. Chim. Acta, 24, 183 (1969)].

(b) Method using p-nitrophenyl-N-acetyl-β-D-glucosaminide as substrate p-Nitrophenol formed by hydrolysis of NAG is allowed to form a color under alkaline condition and the color is subjected to colorimetry [Clin. Chem., 27, 1180 (1981)].

(c) Method using sodio-m-cresolsulfonephthaleinyl-N-acetyl-β-D-glucosaminide as substrate m-Cresolsulfonephthalein formed by hydrolysis of NAG is allowed to form a color under alkaline condition and the color is colorimetrically measured [Clin. Chem., 29, 1713 (1983)].

(d) Method using 2-chloro-4-nitrophenyl-N-acetyl-βB-D-glucosaminide as substrate A yellow hue of 2-chloro-4-nitrophenol formed by hydrolysis of NAG is colorimetrically measured at wavelength of about 400 nm [Clin. Chem., 34, 2140 (1988) 3.

(e) Method using sodio-3,3'-dichlorophenolsulfone-phthaleinyl-N-acetyl-β-D-glucosaminide as substrate Chlorophenol red formed by hydrolysis of NAG is colorimetrically measured as such at a wavelength of 575 nm [Japanese Patent KOKAI (Laid-Open) No. 63-309199].

(f) Method for treating with oxidase N-acetylglucosamine formed by NAG using p-nitrophenyl-N-acetyl-β-D-glucosaminide as substrate N-acetyl-β-D-glucosamine oxidase is acted on N-acetylglucosamine formed by hydrolysis of NAG to generate hydrogen peroxide; this hydrogen peroxide is reacted with a color forming agent in the presence of peroxidase and the resulting green dye is colorimetrically measured at 755 nm [KIKI/SHIYAKU (Device and Reagent), 13, 887 (1990)].

However, the methods encounter various problems and cause inconvenience in measurement and inaccuracy in measurement data. For example, in method (a), a special equipment such as a fluorophotometer is required for the measurement. In method (b), a blank sample is required and in addition, after reacting in an acidic region which is optimum pH of NAG, p-nitrophenol as a chromophore is not colored unless the system is made alkaline with sodium hydroxide aqueous solution, etc., which makes it impossible to perform rate assay considered to be most appropriate for determination of enzyme activity. Furthermore, the wavelength used for measurement is at about 400 nm so that the method tends to be readily affected by biological components such as bilirubin or hemolytic hemoglobin in body fluids to cause error in measurement data. In method (c), it is necessary that m-cresolsulfonephthalein formed by hydrolysis of NAG should be measured in an alkaline region as in method (b) and as the result, rate assay cannot be performed. In method (d), no color forming reaction is required so that rate assay may be performed. However, 2-chloro-4-nitro-phenyl-N-acetyl-β-D-glucosaminide as substrate is sparingly soluble in water so that a surface-active agent is needed to dissolve the substrate; even so, several minutes are required to completely dissolve the substrate. In addition, since the wavelength used for measurement is at about 400 nm, the method is readily affected by biological components as in method (b). In method (e), rate assay can be made. However, pKa (pKa= −log Ka, wherein Ka is acid dissociation constant) of chlorophenol red which is the hydrolysate is 5.8 so that dissociation is insufficient even at a pH for measurement (6.0). Thus, its molecular extinction coefficient changes by slight change of pH in the solution. For this reason, the method involves a problem that error is easily caused in measurement. Furthermore, stability after dissolution of the substrate is only a week when stored in a refrigerator, which would be a problem in view of user's requirement for reagents usable over a long period of time. This stability after dissolution of substrate is less than a week also in methods (a), (c) and (d) and is a defect common to these methods as in method (e). Method (f) is also applicable to rate assay. Due to the use of oxidase, however, the method is affected by reducing substances such as bilirubin or substances co-present in the reaction system such as hemoglobin, metal, sugar, etc. when they are present in a high concentration. In addition, stability after preparation of reagent is also for about 2 weeks and not always satisfactory.

As a result of extensive investigations to solve these problems in the prior art, the present inventors have reached the present invention. That is, novel compounds represented by general formula (I) were synthesized to investigate a method for assaying NAG activity by UV rate assay, using such compounds as substrates. It has thus been found that a wavelength in the range of 320 to 380 nm can be used in this method and the substrate solution is extremely stable to non-enzymatic hydrolysis. By using the substrates, NAG activity in body fluids can be accurately determined in a simple manner in a short period of time without being affected by biological components. In addition, the method is also advantageous in various aspects that the solubility of substrates is good and when stored in a refrigerator, the substrate solution can be stored over a long period of time for at least one month.

SUMMARY OF THE INVENTION

That is, the present invention relates to novel N-acetyl-β-D-glucosamine derivatives represented by general formula (I):

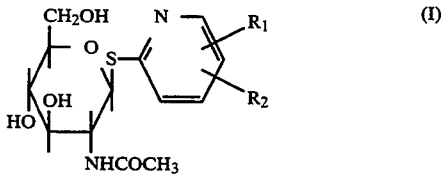

wherein each of $R_1$ and $R_2$ independently represents hydrogen atom or methyl or ethyl group. The present invention also relates to a method for assaying N-acetyl-β-D-glucosaminidase activity using the N-acetyl-β-D-glucosamine derivatives as substrates.

A first aspect of the present invention lies in the N-acetyl-β-D-glucosamine derivatives represented by general formula [I] described above.

A second aspect of the present invention lies in a method for determination of N-acetyl-β-D-glucosaminidase activity which comprises mixing a sample containing N-acetyl-β-D-glucosaminidase with an N-acetyl-β-D-glucosamine derivative and then measuring absorbance of the reaction solution.

BRIEF DESCRIPTION OF THE DRAWINGS

FIG. 9 shows stability of 6MePT-NAG substrate solution when stored in a refrigerator over 30 days and also shows absorbance of substrate blank.

DETAILED DESCRIPTION OF PREFERRED EMBODIMENTS

Figure 1:
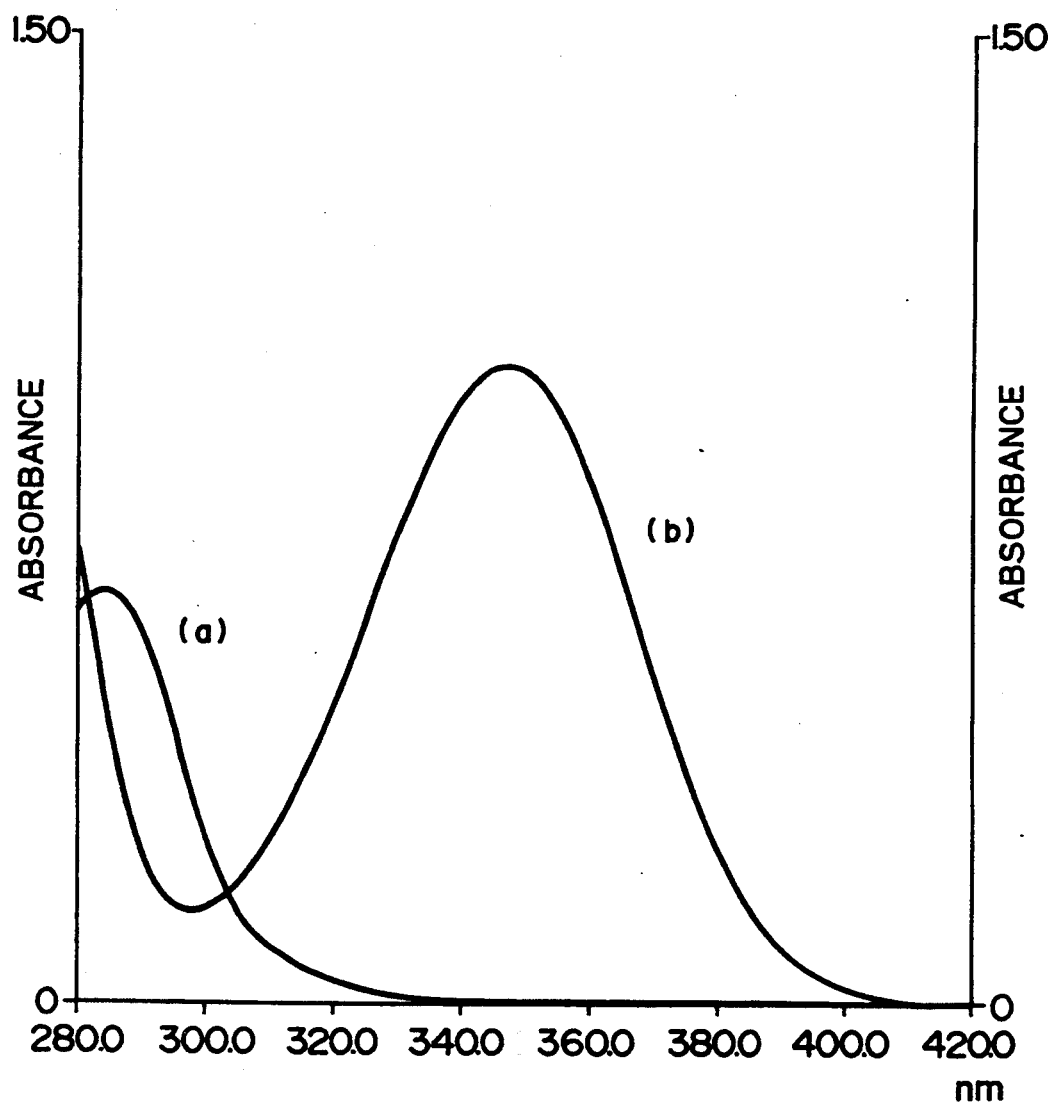
FIG. 1 shows UV spectra of (a) 6MePT-NAG (0.1 mM) and (b) 6-methyl-2-pyridinethiol (0.1 mM) in 100 mM citrate buffer solution (pH 4.5) (25° C.).

The novel N-acetyl-β-D-glucosamine derivatives used as substrates are hydrolized by the action of NAG to liberate 2-pyridinethiol derivatives represented by general formula (II) given below. The liberated 2-pyridinethiol derivatives show spectrum absorption different from that of the substrate.

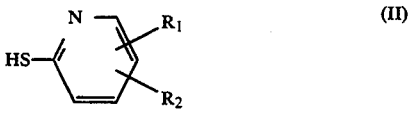

wherein each of $R_1$ and $R_2$ independently represents hydrogen atom or methyl or ethyl group.

Examples of such 2-pyridinethiol derivatives include 2-pyridinethiol, 3-methyl-2-pyridinethiol, 4-methyl-2-pyridinethiol, 5-methyl-2-pyridinethiol, 6-methyl-2-pyridinethiol, 3-ethyl-2-pyridinethiol, 4-ethyl-2-pyridinethiol, 5-ethyl-2-pyridinethiol, 6-ethyl-2-pyridinethiol, 3,4-dimethyl-2-pyridinethiol, 3,5-dimethyl-2-pyridinethiol, 3,6-dimethyl-2-pyridinethiol, 4,5-dimethyl-2-pyridinethiol, 4,6-dimethyl-2-pyridinethiol, 5,6-dimethyl-2-pyridinethiol, 3,4-diethyl-2-pyridinethiol, 3,5-diethyl-2-pyridinethiol, 3,6-diethyl-2-pyridinethiol, 4,5-diethyl-2-pyridinethiol, 4,6-diethyl-2-pyridinethiol, 5,6-diethyl-2-pyridinethiol, 3-ethyl-4-methyl-2-pyridinethiol, 3-ethyl-5-methyl-2-pyridinethiol, 3-ethyl-6-methyl-2-pyridinethiol, 4-ethyl-5-methyl-2-pyridinethiol, 4-ethyl-6-methyl-2-pyridinethiol, 5-ethyl-6-methyl-2-pyridinethiol, 4-ethyl-3-methyl-2-pyridinethiol, 5-ethyl-3-methyl-2-pyridinethiol, 6-ethyl-3-methyl-2-pyridinethiol, 5-ethyl-4-methyl-2-pyridinethiol, 6-ethyl-4-methyl-2-pyridinethiol, 6-ethyl-5-methyl-2-pyridinethiol, etc.

The novel N-acetyl-β-D-glucosamine derivatives can be easily synthesized, e.g., according to the reaction scheme shown below.

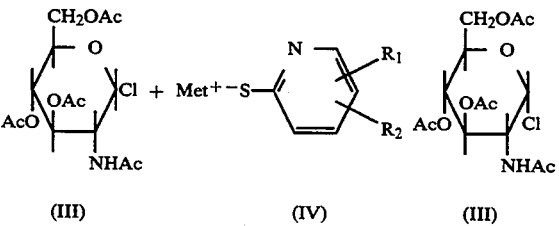

-continued

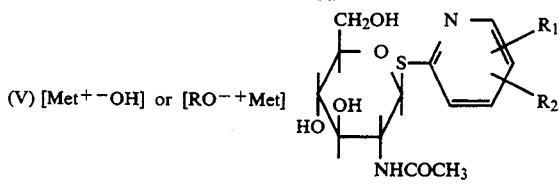

(I)

wherein Ac represents acetyl group; Met represents an alkali metal; R represents an alkyl group; and each of $R_1$ and $R_2$ independently represents hydrogen atom, methyl or ethyl group.

That is, Compound (V) can be obtained by coupling known 1-chloro-1-deoxy-2,3,4,6-tetraacetyl-α-D-glucosamine (III) described in Org. Syn., 46, 1 (1966), etc. with salts (IV) of alkali metals such as sodium, potassium etc. of 2-pyridinethiol derivatives in a solvent such as acetone, dimethylformamide (DMF), etc. to form S-glycoside bond. In addition, Compound (V) may also be obtained by directly reacting Compounds (II) and (III) in the presence of a base. Any other conventional methods which can form glycoside bond may also apply to the reaction in the present invention.

Then, an alkali such as metal hydroxides [Met $OH^{+-}$] such as potassium hydroxide or metal alcoholates [$RO^{-+}OH$] such as sodium methylate or sodium ethylate is reacted with Compound (V) to split O-acetyl group off, whereby Compound (I) of the present invention can be obtained. These reactions are all known per se and the reaction conditions are similar to those in the known reactions.

Turning next to the method for determination of NAG activity of the present invention using the novel N-acetyl-β-D-glucosamine derivatives, the method is described by referring to 6-methyl-2-pyridyl-N-acetyl-1-thio-β-D-glucosaminide (hereafter abbreviated as 6MePT-NAG).

FIG. 1 shows UV spectra of (a) 6MePT-NAG and (b) 6-methyl-2-pyridinethiol in acidic buffer solution (pH 4.5).

Upon hydrolysis of 6MePT-NAG by the action of NAG, N-acetyl-D-glucosamine and 6-methyl-2-pyridinethiol are formed. Both N-acetyl-D-glucosamine and 6MePT-NAG have no substantial UV absorption at wavelength longer than 320 nm. 6-Methyl-2-pyridinethiol absorbs UV below 380 nm. Accordingly, in the method of assaying NAG activity by UV rate assay, the reaction can be traced at a measurement wavelength in the range of 320 to 380 nm, using 6MePT-NAG as substrate; in this case, interference by other biological components is minimized. Therefore, increase of 6-methyl-2-pyridinethiol can be accurately traced and NAG activity can be determined accurately. In addition, 6MePT-NAG has many advantages as will be later described.

Accordingly, as the method for assaying NAG activity using the novel N-acetyl-β-D-glucosamine derivatives of general formula (I), for example, the following method is specifically provided. That is, a sample containing NAG is mixed with the novel N-acetyl-β-D-glucosamine derivatives represented by general formula (I) and then absorbance, especially absorbance in the range of 320 to 380 nm is measured thereby to assay NAG activity.

In method (d) described above using 2-chloro-4-nitrophenyl-N-acetyl-β-D-glucosaminide as substrate, rate assay can be performed in an acidic region which is the optimum pH of NAG but the measurement wavelength is at about 400 nm so that the measurement data is seriously interfered by biological components such as bilirubin or hemoglobin; whereas in the present invention, the data is not substantially affected at the measurement wavelength in the range of 320 to 380 nm so that the optimum conditions for measurement can be readily set forth. In addition, when the novel N-acetyl-β-D-glucosamine derivatives of the present invention, e.g., 6MePT-NAG is hydrolyzed, the resulting 6-methyl-2-pyridinethiol has the absorption maximum at about 340 nm so that the measurement wavelength can be set forth at the peak. This indicates that difference in molecular extinction coefficient generated from accuracy in wavelength of an analytical device becomes very small and difference in measurement data depending upon type of an analytical device becomes very small.

Furthermore, the novel substrate of the present invention is readily soluble in water. This means that it is unnecessary to add any surface active agent for dissolving the substrate, unlike the aforesaid substrate, e.g., 2-chloro-4-nitrophenyl-N-acetyl-β-D-glucosaminide. Accordingly, by using the substrate of the present invention, the substrate solution can be prepared in an extremely simple manner in a short period of time.

The substrate solution of the present invention is extremely stable to non-enzymatic hydrolysis. For example, NAG activity of the same sample was intermittently assayed over 30 days using 6MePT-NAG solution stored in a refrigerator; no significant change in measurement data was noted (cf. FIG. 8) and increase in reagent blank was also slight and within the range that did not decrease the measurement limit (cf. FIG. 9). This indicates that when 6MePT-NAG is used as substrate, the substrate solution can be used over such a long period of time as at least one month when it is stored in a refrigerator after preparation, unlike conventional substrate.

Upon assaying NAG activity using the substrate of the present invention, citric acid, acetic acid, succinic acid, phthalic acid and other salts may be used as buffers for maintaining a pH on a constant level. Other buffers may also be used so long as they can maintain buffering function at pH between 3.0 and 7.0. In addition, the reagents of the present invention may also contain, if necessary and desired, a stabilizer, a dissolution aid, an antiseptic, etc. Examples of such additives include cyclodextrins, bovine serum albumin, salts such as disodium EDTA or sodium chloride, surface active agents such as Triton X-100, etc.

The method for determination of NAG activity according to the present invention can eliminate various problems involved in the prior art. Advantages of the present invention are given below.

(1) The wavelength for measurement can be set forth in UV region from 320 to 380 nm so that the method is interfered only with difficulty by substances co-present in biological components such as billirubin or hemoglobin.

(2) Measurement can be performed at the peak wavelength (340 nm) so that error in measurement data is minimized.

(3) The solubility of the substrate in water is excellent so that it is easy to prepare a substrate solution.

(4) The substrate solution is stable and can be used for measurement over a long period of time when stored in a refrigerator.

(5) Rate assay can be performed so that the method is readily applicable to an automated analytical device.

As stated above, the method for determination of NAG activity of the present invention can solve the problems encountered in the prior art, provides many advantages and characteristics, can determine NAG activity accurately in a simple manner and can sufficiently contribute to determination of NAG activity in ordinary clinical test.

Hereafter the present invention is described in more detail, by referring to examples but is not deemed to be limited thereto.

EXAMPLE 1

Synthesis of 6-methyl-2-pyridyl-N-acetyl-1-thio-$\beta$-D-glucosaminide

After 20 ml of dimethylformamide (DMF) was added to 1.47 g (10.0 mmols) of 6-methyl-2-pyridinethiol sodium salt and 4.39 g (12.0 mmols) of 1-chloro-1-deoxy-2,3,4,6-tetraacetyl-$\beta$-D-glucosamine, the mixture was reacted at room temperature for 48 hours while stirring. After completion of the reaction, 100 ml of chloroform was added to the reaction solution. After washing with distilled water 3 times, the mixture was dried over anhydrous magnesium sulfate. The solvent was distilled off under reduced pressure. The resulting light yellow crystals were dissolved in methanol and ether was added to the solution to recrystallize. Thus, 1.50 g (yield 31%) of 6'-methyl-2'-pyridyl-2,3,4,6-tetraacetyl-1-thio-$\beta$-D-glucosaminide was obtained as white cotton-like crystals.

Melting point: 145° C. (decomposed)
Elemental analysis: as $C_{20}H_{26}N_2O_8 \cdot CH_3OH$
Found % (calcd. %)
C: 51.81 (51.84), H: 5.91 (6.21),
N: 5.61 (5.76)

Next, 1.45 g (3.0 mmols) of 6'-methyl-2'-pyridyl-2,3,4,6-tetraacetyl-1-thio-$\beta$-D-glucosaminide was dissolved in 40 ml of anhydrous methanol and 0.148 ml (0.8 mmol) of 28% sodium methylate was added to the solution while stirring. The mixture was stirred for an hour under cooling on an ice bath. After it was confirmed by thin layer chromatography that the reaction was completed, 0.5 ml of Amberlist™ 15E which is cationic exchange resin was added to the reaction solution. The mixture was stirred for further 20 minutes to neutralize the unreacted sodium methylate. The resin was filtered off and the liltrate was concentrated under reduced pressure to give white crystals. The crystals were recrystallized from methanol to give 0.75 g (yield 60%) of 6-methyl-2-pyridyl-N-acetyl-1-thio-$\beta$-D-glucosaminide as white powders.

Melting point: 165° C. (decomposed)
Elemental analysis: as $C_{14}H_{20}N_2O_5S \cdot 3/2 CH_3OH$
Found % (calcd. %)
C: 49.57 (49,45), H: 6.90 (6.96),
N: 7.55 (7.47)

Figure 2:
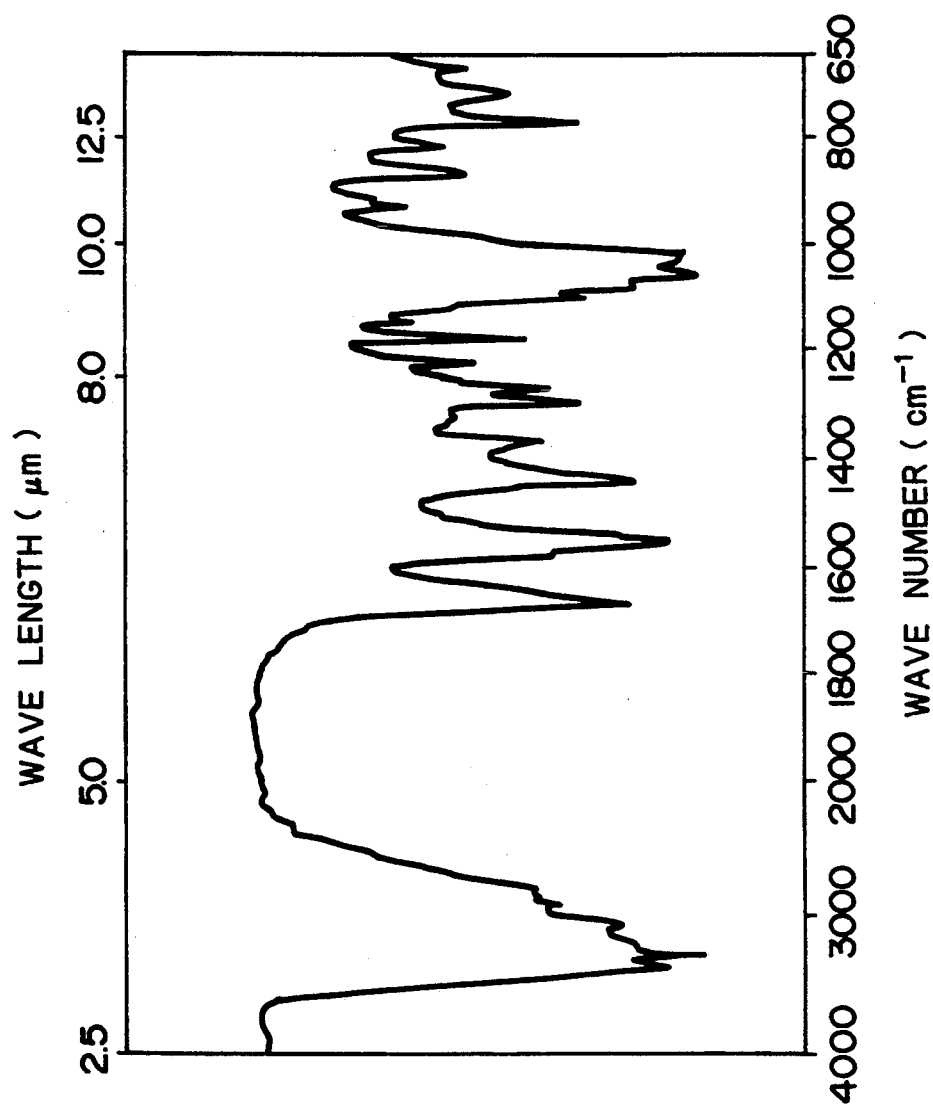
FIG. 2 shows IR spectrum of 6MePT-NAG in potassium bromide.

UV spectrum and IR spectrum are shown in FIGS. 1 and 2, respectively.

EXAMPLE 2

Synthesis of 6-ethyl-2-pyridyl-N-acetyl-1-thio-$\beta$-D-glucosaminide

After 20 ml of dimethylformamide (DMF) was added to 1.20 g (7.5 mmols) of 6-ethyl-2-pyridinethiol sodium salt and 3.42 g (9.3 mmols) of 1-chloro-1-deoxy-2,3,4,6-tetraacetyl-$\beta$-D-glucosamine, the mixture was reacted at room temperature for 48 hours while stirring. After completion of the reaction, 100 ml of chloroform was added to the reaction solution. After washing with distilled water 3 times, the mixture was dried over anhydrous magnesium sulfate. The solvent was distilled off under reduced pressure. The resulting light yellow crystals were recrystallized from hot methanol to give 1.21 g (yield 35%) of 6'-ethyl-2'-pyridyl-2,3,4,6-tetraacetyl-1-thio-$\beta$-D-glucosaminide which was obtained as white cotton-like crystals.

Melting point: 193°–196° C. (decomposed)
Elemental analysis: as $C_{21}H_{28}N_2O_8S$
Found % (calcd. %)
C: 53.63 (53.84), H: 6.18 (6.02),
N: 5.83 (5.98)

Next, 1.20 g (2.6 mmols) of 6'-ethyl-2'-pyridyl-2,3,4,6-tetraacetyl-1-thio-$\beta$-D-glucosaminide was dissolved in 30 ml of anhydrous methanol and 0.119 ml (0.6 mmol) of 28% sodium methylate was added to the solution while stirring. The mixture was stirred for 45 minutes under cooling on an ice bath. After it was confirmed by thin layer chromatography that the reaction was completed, 0.5 ml of Amberlist™ 15E which is cationic exchange resin was added to the reaction solution. The mixture was stirred for further 20 minutes to neutralize the unreacted sodium methylate. The resin was filtered off and the liltrate was concentrated under reduced pressure to give white crystals. The crystals were recrystallized from methanol to give 0.60 g (yield 63% of 6-ethyl-2-pyridyl-N-acetyl-1-thio-$\beta$-D-glucosaminide as white powders.

Melting point: 170° C. (decomposed)
Elemental analysis: as $C_{15}H_{22}N_2O_5S \cdot CH_3OH$
Found % (calcd. %)
C: 51.71 (51.32), H: 6.65 (7.00),
N: 7.73 (7.48)

Figure 3:
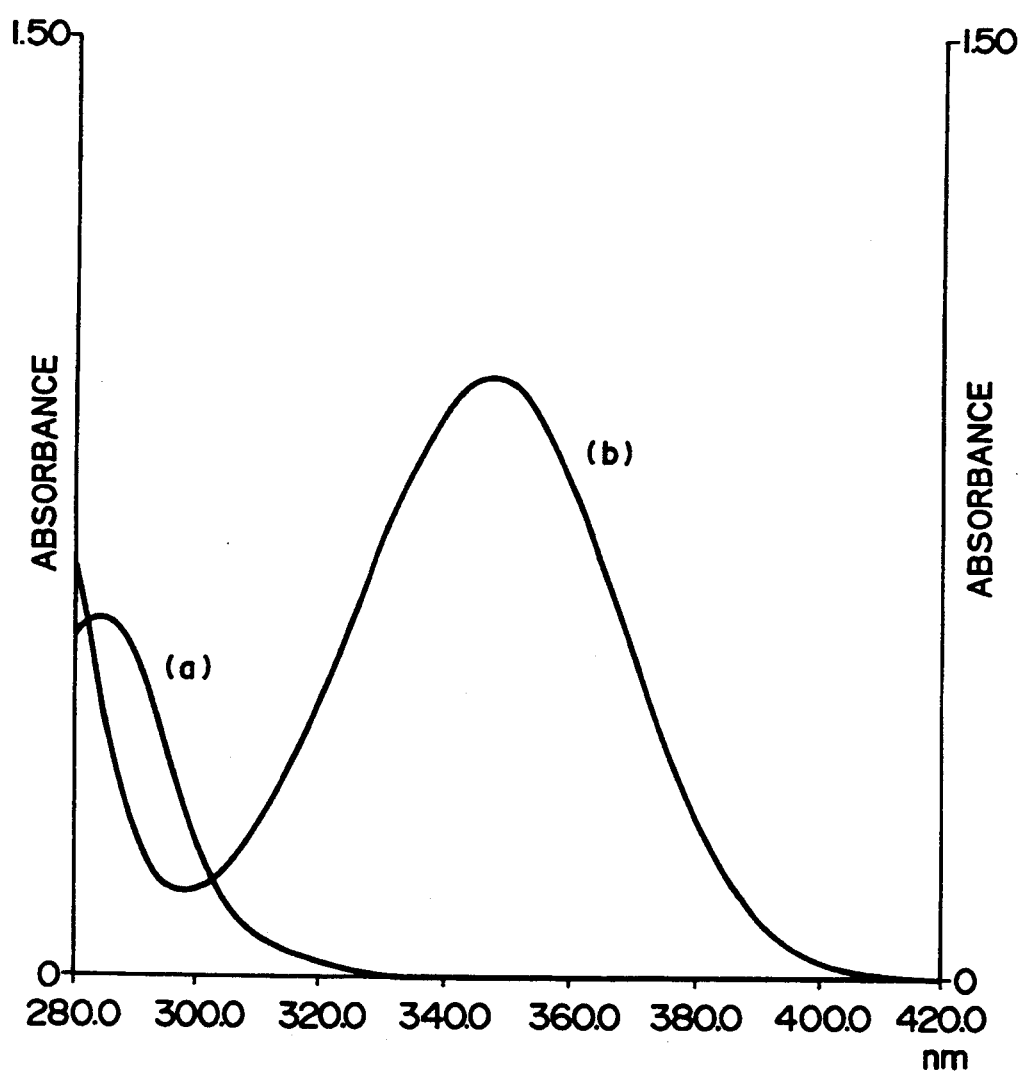
FIG. 3 shows UV spectra of (a) 6EtPT-NAG (0.1 mM) and (b) 6-ethyl-2-pyridinethiol (0.1 mM) in 100 mM citrate buffer solution (pH 4.5) (25° C.).
Figure 4:
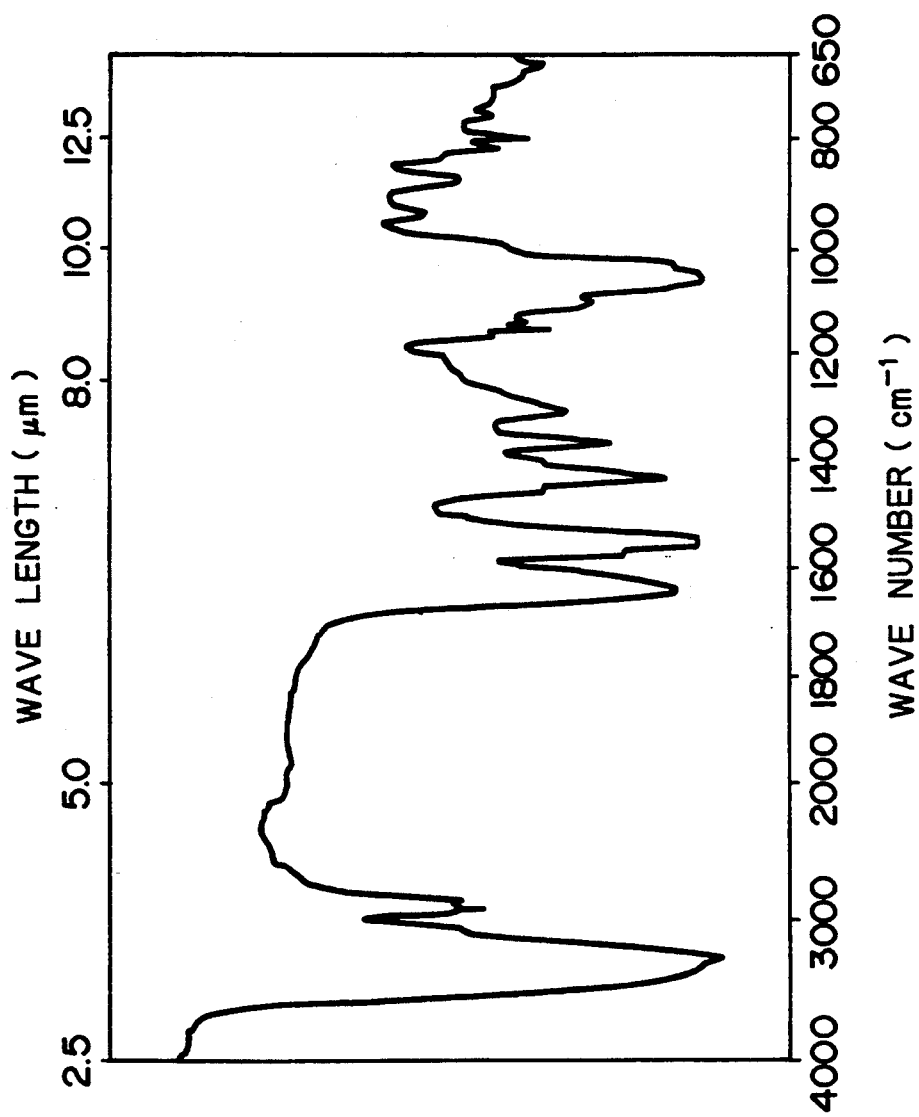
FIG. 4 shows IR spectrum of 6EtPT-NAG in potassium bromide.

UV spectrum and IR spectrum are shown in FIGS. 3 and 4, respectively.

EXAMPLE 3

The structures of the compounds of the present invention synthesized in a manner similar to the respective examples described above and melting points (decomposition points) thereof as well as elemental analysis are shown in Table 1. However, the present invention is not deemed to be limited only to these compounds.

TABLE 1

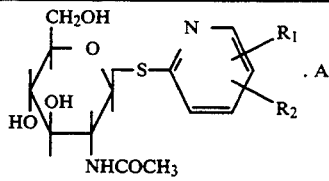

| R₁ Position | R₁ Substituent | R₂ Position | R₂ Substituent | A | Melting point (°C.) | Found (%) C | Found (%) H | Found (%) N | Calcd. (%) C | Calcd. (%) H | Calcd. (%) N |
|---|---|---|---|---|---|---|---|---|---|---|---|
| 6 | CH₃ | | H | 3/2CH₃OH | 165 (deg) | 49.57 | 6.90 | 7.55 | 49.45 | 6.96 | 7.47 |
| 5 | CH₃ | | H | 1/2CH₃OH | 182 (deg) | 50.69 | 6.23 | 8.23 | 50.57 | 6.44 | 8.13 |
| 4 | CH₃ | | H | 7/10H₂O | 172 (deg) | 49.28 | 6.21 | 8.15 | 49.31 | 6.33 | 8.22 |
| 3 | CH₃ | | H | — | 179 (deg) | 51.03 | 6.33 | 8.27 | 51.21 | 6.14 | 8.53 |
| 6 | CH₃ | 4 | CH₃ | CH₃OH | 160 (deg) | 50.93 | 7.19 | 7.29 | 51.32 | 7.00 | 7.48 |
| 6 | C₂H₆ | | H | CH₃OH | 175 (deg) | 51.71 | 6.65 | 7.73 | 51.32 | 7.00 | 7.48 |
| 4 | C₂H₆ | | H | 1/2CH₃OH | 150 (deg) | 51.59 | 6.59 | 7.92 | 51.94 | 6.75 | 7.82 |

EXAMPLE 4

Determination of NAG activity using 6-methyl-2-pridyl-N-acetyl-1-thio-β-D-glucosaminide (6MePT-NAG)

(1) 100 mM citrate buffer solution: pH 4.50 (25° C.)
(2) Sample
(3) 17.4 mM substrate (6MePT-NAG) solution The substrate solution was prepared by accurately weighing 32.84 mg of 6MePT-NAG and dissolving 6MePT-NAG in 5 ml of purified water. In this case, 6MePT-NAG was rapidly dissolved in one minute.

Figure 5:
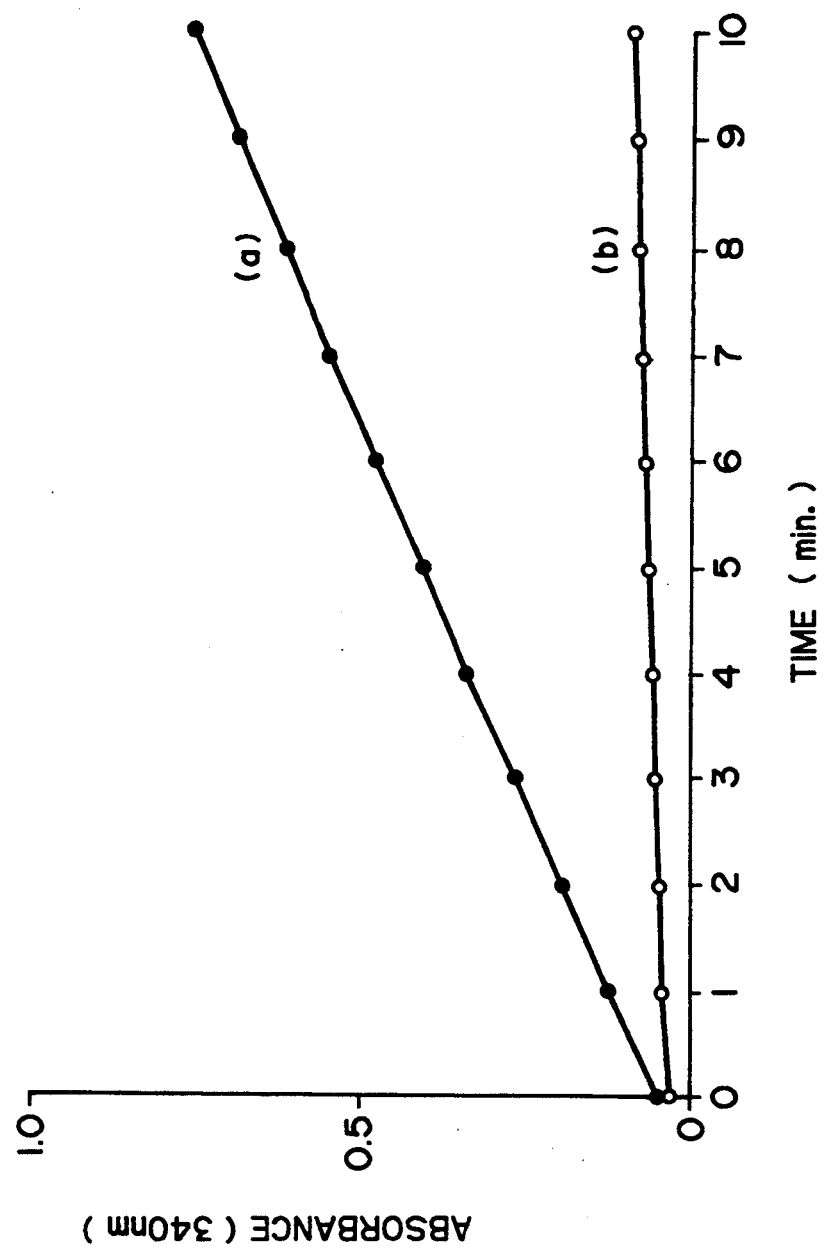
FIG. 5 shows a reaction time course when 6MePT-NAG was used as substrate and (b) time course of substrate blank.

The procedures for the measurement are as follows. After 0.1 ml of the sample is added to 2.0 ml of buffer solution (1), the mixture is preheated at 37° C. for 3 minutes and 0.5 ml of substrate solution (3) is added thereto. At the same time, a stop watch starts and absorbance at 340 nm is measured accurately every 1 minute to determine change in absorbance per minute. FIG. 5 shows its time course.

As the sample, bovine kidney-derived NAG (manufactured by Sigma Co., Ltd.) diluted with 10 mM citrate buffer (pH 6.0) is used. (a) indicates its time course and (b) shows a time course of substrate blank added with physiological saline, instead of the sample. The NAG activity is calculated by the following equation:

$$IU/L = \frac{(\Delta Ea - \Delta Eb)^{1)} \times \text{total volume of reaction solution} \times 10^6}{\text{molecular extinction coefficient}^{2)} \times \text{volume of sample}} \quad (a)$$

[1] ΔEa and ΔEb mean a change in absorbance of sample and substrate blank per minute at the measurement wavelength of 340 nm.
[2] Molecular extinction coefficient of 6-methyl-2-pyridinethiol at the wavelength of 340 nm is 9029 (1·mol⁻¹·cm⁻¹).

Based on the above equation, NAG activity of the solution used was 184 IU/L. As shown in FIG. 5, the time course showed linearity for 10 minutes with passage of time. This indicates that the method is applicable to an automated analytical device.

EXAMPLE 5

Determination of NAG activity using 6-ethyl-2-pyridyl-N-acetyl-1-thio-β-D-glucosaminide (6EtPT-NAG)

Figure 6:
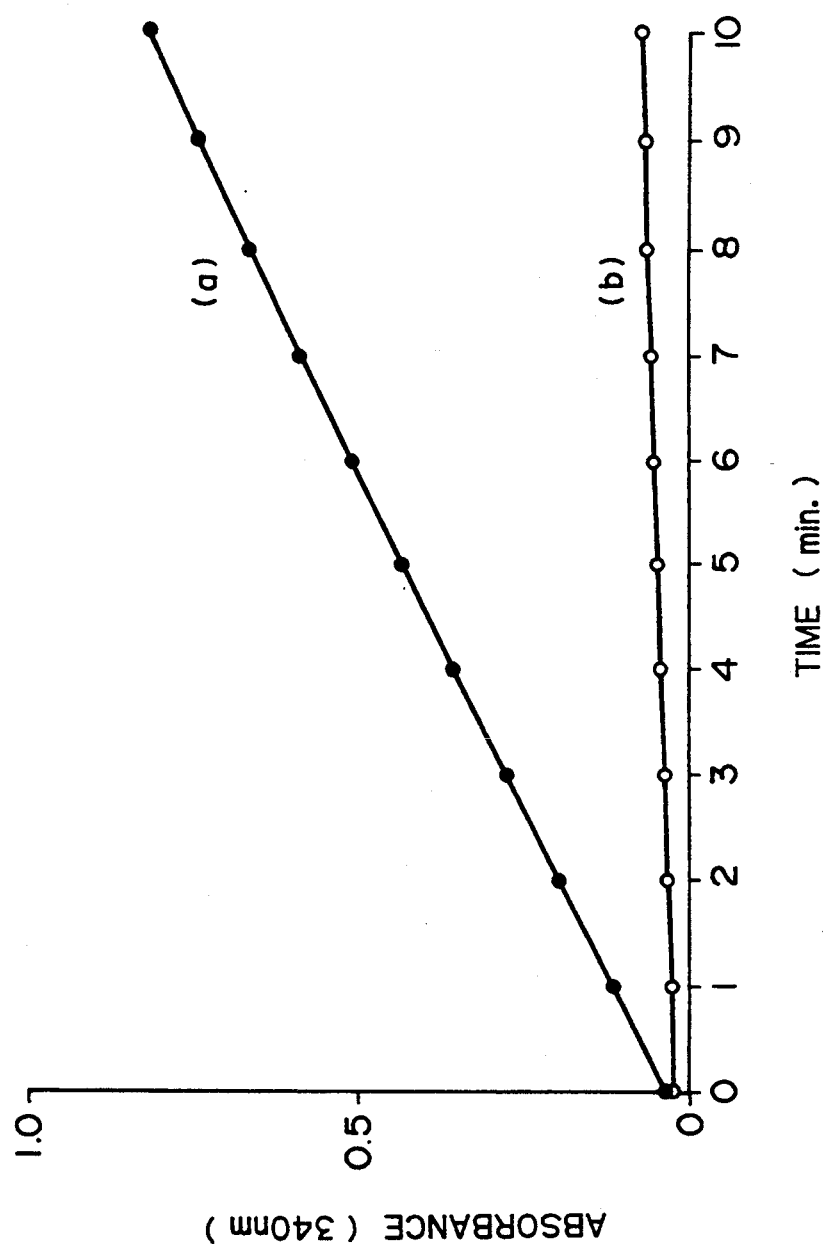
FIG. 6 shows a reaction time course when 6EtPT-NAG was used as substrate and (b) time course of substrate blank.

The NAG activity of a sample was determined in a manner similar to Example 3 using the buffer solution (1) and the sample (2) in Example 4, except that 17.4 mM 6EtPT-NAG was used instead of the substrate (3). FIG. 6 shows its time course, wherein (a) is the sample and (b) is the substrate blank.

Based on the equation (a) in Example 3, the NAG activity of the sample used was 180 IU/L [molecular extinction coefficient of 6-ethyl-2-pyridyl-N-acetyl-β-D-glucosaminide was 9244 (1 mol⁻¹ cm⁻¹)]. As shown in FIG. 6, even when 6EtPT-NAG was used as substrate, the time course showed linearity for 10 minutes with passage of time. Accordingly, this case is also applicable to an automated analytical device.

EXAMPLE 6

Figure 7:
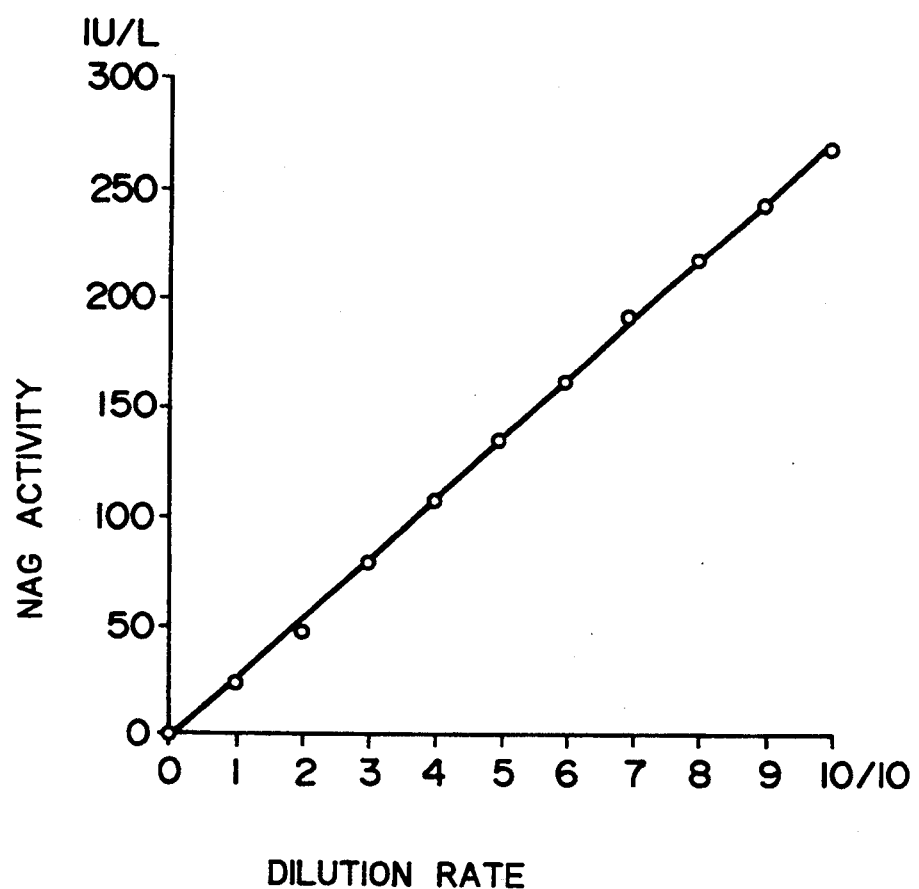
FIG. 7 shows relationship between NAG dilution and enzyme activity.

Following Example 4, relationship between dilution rate of bovine kidney-derived NAG and enzyme activity was examined. A sample was diluted with 10 mM citrate buffer solution (pH 6.0). As shown in FIG. 7, sample dilution and enzyme activity are in a linear proportional relationship which passes the original point. The results reveal that NAG activity can be assayed over a wide range from a low unit to a high unit.

EXAMPLE 7

Bovine kidney-derived NAG was diluted with 10 mM citrate buffer solution (pH 6.0) and the dilution was divided into aliquots followed by lyophilization in a freezing room at −20° C. The sample was measured 6 times in total on the day when the substrate solution was prepared and Days 2, 7, 15, 22 and 30, using the 6MePT-NAG substrate solution (3) in Example 4. The substrate solution was stored in a refrigerator at 2° to 8° C. According to Medical Technology, 19, 6 (1991), NAG activity was stable for about one month in a solution showing pH of about 6.0 when stored in a frozen state.

Figure 8:
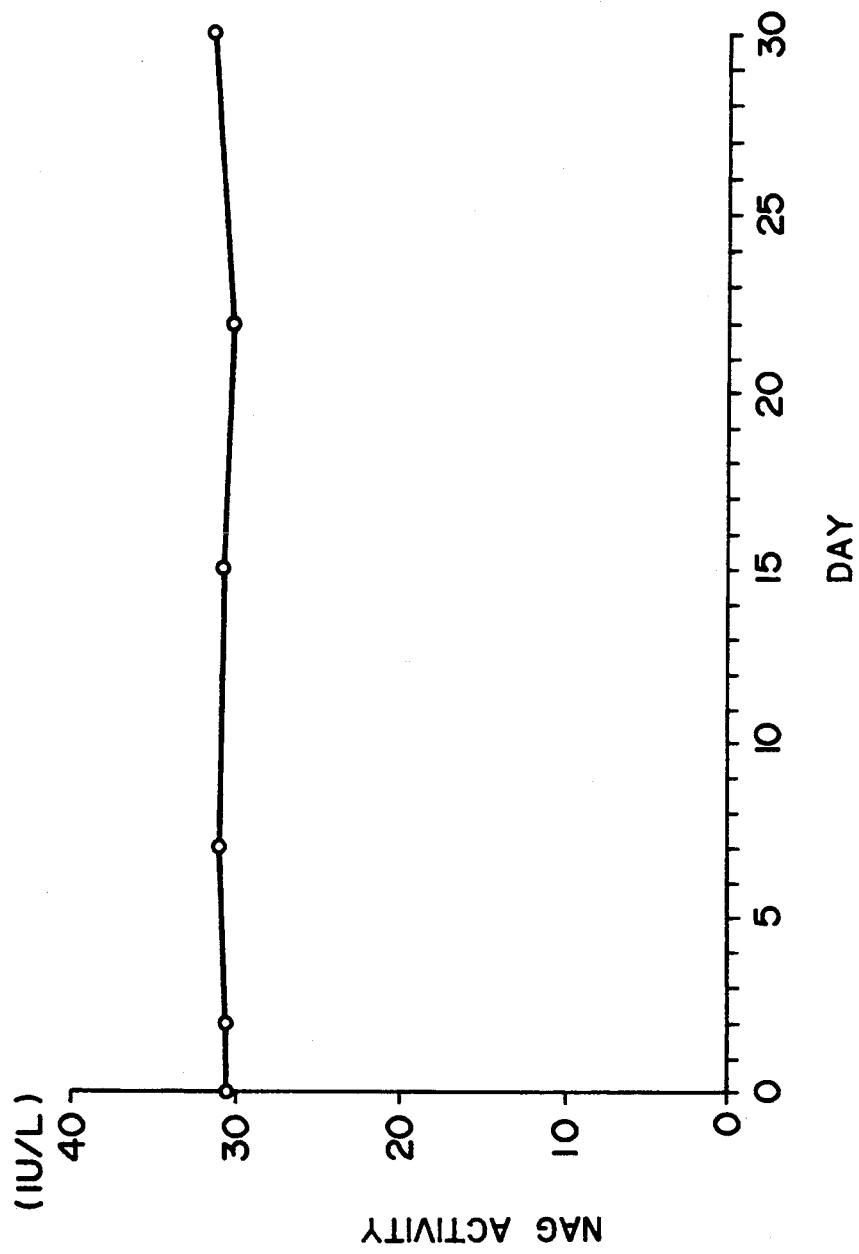
FIG. 8 shows stability of 6MePT-NAG substrate solution when stored in a refrigerator over 30 days and also shows NAG activity level (change in day) measured.

FIG. 8 shows the measurement data and FIG. 9 shows change in absorbance of substrate blank. These figures reveal that the substrate solution of the present invention is usable for at least one month when stored in a refrigerator (2° to 8° C.) after preparation.

What is claimed is:

1. A method for the determination of N-acetyl-β-D-glucosaminidase activity in a sample which comprises mixing a sample containing N-acetyl-β-D-glucosaminidase with an N-acetyl-β-D-glucosamine derivative to form a reaction solution, said derivative defined by the general formula I,

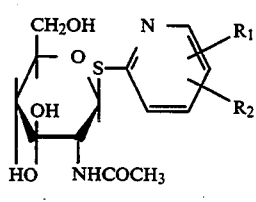

wherein each of $R_1$ and $R_2$ independently represents a hydrogen or a methyl group or ethyl group; and determining the activity present by measuring changes in the UV absorbance of the reaction solution at a wavelength of 320–380 nm.

2. A method as in claim 1, wherein said reaction mixture contains a citrate buffer at pH 4.5 and is held at 37° C. prior to measurement of absorbance.

3. A method according to claim 1, wherein the method is conducted by an automated analytical device.

4. A method according to claim 1, wherein said sample is human urine.

5. A method according to claim 1, wherein said derivative is 6-methyl-2-pyridyl-N-acetyl-1-thio-β-D-glucosaminide.

6. A method for the determination of N-acetyl-β-D-glucosaminidase activity which comprises mixing a human urine sample containing N-acetyl-β-D-glucosaminidase with 6-methyl-2-pyridyl-N-acetyl-1-thio-β-D-glucosaminide to form a reaction solution; and measuring UV absorbance of the reaction solution at a wavelength of 320–380 nm.

* * * * *